(12) United States Patent
Kulmann

(10) Patent No.: US 7,871,994 B2
(45) Date of Patent: Jan. 18, 2011

(54) HORMONE REPLACEMENT THERAPY METHOD AND ITS ADMINISTRATION FORM

(75) Inventor: Hermann Kulmann, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 1981 days.

(21) Appl. No.: 10/466,197

(22) PCT Filed: Jan. 8, 2002

(86) PCT No.: PCT/EP02/00089

§ 371 (c)(1),
(2), (4) Date: Jan. 14, 2004

(87) PCT Pub. No.: WO02/055086

PCT Pub. Date: Jul. 18, 2002

(65) Prior Publication Data

US 2004/0106586 A1    Jun. 3, 2004

(30) Foreign Application Priority Data

Jan. 11, 2001    (DE) ................................ 101 00 911

(51) Int. Cl.
*A61K 31/56*    (2006.01)
(52) U.S. Cl. ...................................... 514/170; 514/182
(58) Field of Classification Search .................. 514/171, 514/170

See application file for complete search history.

(56) References Cited

U.S. PATENT DOCUMENTS

RE36,247 E * 7/1999 Plunkett et al. ............. 514/170
5,980,940 A    11/1999 Spona et al.

FOREIGN PATENT DOCUMENTS

| DE | 19539233 | 4/1997 |
| WO | WO 94/02103 | 2/1994 |
| WO | WO 95/22332 | 7/1995 |
| WO | WO 95/22334 | 7/1995 |

OTHER PUBLICATIONS

Teather et al., Journal of Bacteriology, 1990;172(7):3837-3841.*
Martindale: 1993, Pharm. Press, London XP002229615, p. 1169-1170.

* cited by examiner

*Primary Examiner*—San-ming Hui
(74) *Attorney, Agent, or Firm*—Millen, White, Zelano & Branigan, P.C.

(57) ABSTRACT

Method for hormone replacement therapy, in which at least in the established postmenopause a daily unit with at least one hormonal component, namely with at least estrogen (E) and/or at least one gestagen (G) is administered permanently and continuously every day, characterized in that in at least one ingestion period preceding the permanent administration of hormone daily units is provided an ingestion pause (P), in which either no daily units or placebos or daily units with a much lower estrogen and/or gestagen content than during the permanent administration of hormone daily units in the established postmenopause and during the ingestion phase(s) of the preceding ingestion period are administered, as well as administration form for hormone therapy.

31 Claims, No Drawings

HORMONE REPLACEMENT THERAPY METHOD AND ITS ADMINISTRATION FORM

The invention relates to a hormone replacement therapy method, in which at least in the established postmenopause administration takes place in a permanent and continuous daily basis of a daily unit of at least one hormonal component, namely with at least one estrogen (E) and/or at least one gestagen (G), as well as an administration form for performing the same, with a plurality of packaging units, whereof at least one has at least one set of hormone daily units to be continuously administered at least in the established postmenopause, in each case having a content of at least one hormonal component, namely at least one estrogen (E) and/or at least one gestagen (G).

In the hitherto known hormone replacement therapies for women ingestion has taken place sequentially, continuously-sequentially or continuously of an estrogen alone, a gestagen alone or a combination of an estrogen and a gestagen. The following notations can be used for a more precise description of the known regimes.

An "E" designates a random estrogen in a predetermined or preset dose, so that the letter "E" is a place holder for information such as "2 mg E2" or "1 mg EE2", and optionally to make this information easier to understand it is placed in round brackets. A "G" designates a random gestagen in a predetermined or preset dose, so that the letter "G" is a place holder for information such as "1 mg CPA" or "0.1 mg LNG", and such information can optionally also be placed in round brackets.

If an estrogen or gestagen is to be taken or ingested on n-m+1 successive days, it is designated "E[m-n] or G[m-n]". For example, "E[1-21]" means the ingestion of a here not further specified estrogen with a predetermined dose over 21 successive days and "(1 mg CPA)[21-28]" means the ingestion on a daily basis of 1 mg of cyproterone acetate (CPA) over 8 successive days.

An ingestion-free period of n-m+1 successive days is designated "P[m-n]" and this also applies for the taking of a placebo. If an estrogen and a gestagen are simultaneously taken, this is designated with overlapping periods. Thus, the expression "E[1-21]G[12-21]" means that on 11 successive days an estrogen alone and on the following 10 days an estrogen and a gestagen are simultaneously taken. It is finally agreed that the first day of a hormone replacement therapy is always designated "1".

The above-given notation clearly describes a regime. However, there are different notation systems for a given regime. Thus, the ingestion of an estrogen over a period of 28 successive days can be designated both E[1-28] and E[1-14]E[15-28].

In the above notation, the hitherto developed regimes can be described as follows:

A sequential estrogen monotherapy can be given in complete notation as E[1-21]P[22-28]E[29-49]P[50-56]E[57-77]P[78-84] and in abbreviated notation as {E[1-21]P[22-28]}.

A continuous estrogen monotherapy can be described in complete notation as E[1-28]E[29-56]E[57-84] and in abbreviation notation as {E[1-28]}.

The known, continuous gestagen monotherapy can be described in complete notation as G[1-28]G[29-56]G[57-84] and in abbreviated notation as {G[1-28]}.

The known, sequential combination therapy can be given in complete notation as E[1-21]G[12-21]P[22-28]E[29-49]G[40-49]P[50-56] and in abbreviated notation as {E[1-21]G[12-21]P[22-28]}.

Sequential-continuous combination therapies, in which the daily dose of E' is lower than the daily dose of E, can be described in complete notation as E[1-21]G[12-21]E[22-28]E[29-49]G[40-49]E[50-56] and in abbreviated notation as {E[1-21]G[12-21]E[22-28]} or E[1-21]G[12-21]E'[22-28]E[29-49]G[40-49]E'[50-56] and in abbreviated notation as {E[1-21]G[12-21]E'[22-28]}.

Finally, a continuous combination therapy can be described in complete notation as E[1-28]G[1-28]E[29-56]E[57-84]G[57-84] and in abbreviated notation as {E[1-28]G[1-28]}.

It must be borne in mind that in the terminology of this patent an ingestion pause not only occurs if no hormone daily unit or placebo is administered, but also if hormone daily units are provided with a much lower estrogen and/or gestagen dose than in the ingestion phases.

Hereinafter and throughout the patent the following abbreviation rules are used. A recurring sequence of ingestion phases or ingestion phases and ingestion pauses is called an ingestion period and its subsequent elements are called ingestion cycles. Ingestion periods can be represented by curly brackets between which appears the first ingestion cycle. Thus, e.g. the regime E[1-21]P[22-28]E[29-49]P[50-56]E[57-77]P[78-84], which consists of only one ingestion period, an also be designated {E[1-21]P[22-28]}. Thus, the expression {E[1-21]P[22-28]} stands for a randomly long sequence of 28 time intervals and in the first 21 days an estrogen is taken and this is followed by a seven day ingestion pause. A fixed number of subsequent elements/ingestion cycles r is designated in that r precedes the expression. Thus, the expression 2{E[1-21] is an abbreviation of the expression E[1-21]E[22-42].

A regime consisting of several ingestion periods is subject to a notation in which the ingestion periods are written in succession. The expression 2{E[1-21]P[22-28]} 1{E1-42]P[43-49]} is consequently an abbreviation of the regime E[1-21]P[22-28]E[29-49]P[50-56]E[57-98]P[99-105].

The hitherto known ingestion regimes have at least in part proved successful, but frequently irregular bleeding occurs in the perimenopause, the length of the menstrual cycles of a woman becoming clearly more variable. It can on the one hand drop to less than 20 days, but on the other can rise to over 40 days. In addition, the number of intermenstrual bleeding can increase and the bleeding intensity can rise. During this period the first menopausal complaints arise.

The problem of the invention is to improve the aforementioned method and administration form in such a way that in particular in the perimenopause a stabilizing of menstruation can be obtained, accompanied by a simultaneous reduction in the menopausal complaints.

In a further development of the aforementioned method, this problem is solved according to the invention in that in at least one ingestion period preceding the permanent administration of hormone daily units an ingestion pause (P) is provided, in which either no daily units or placebos or daily units with a much lower estrogen and/or gestagen content than during the permanent administration of hormone daily units in the established postmenopause and during the ingestion phase(s) of the aforementioned ingestion period are administered.

The permanent administration of hormone daily units can be preceded by at least two ingestion periods when the ingestion phases are successively extended between individual ingestion periods.

It can also be provided that the permanent administration of hormone daily units is preceded by three ingestion periods, in which the ingestion phases are successively extended between individual ingestion periods.

It is also possible for the ingestion periods preceding each permanent administration of hormone daily units to comprise a maximum of two ingestion cycles with in each case one ingestion phase and in each case one ingestion pause.

Moreover, it can be provided that essentially as from the start of the perimenopause in a plurality of substantially time-unlimited, optionally multiyear sequence of successive, following ingestion periods, in each case of at least one ingestion cycle with a multiday, duration-constant ingestion phase within the particular ingestion period and a multiday ingestion pause, in the particular ingestion phase(s) per day administration takes place of a daily unit with at least one hormone component, namely at least one estrogen and/or at least one gestagen and in the ingestion pause(s) administration either takes place of hormone component-free placebos or daily units with a much lower hormone content than during the ingestion phase(s), or the ingestion pause remains completely administration-free and the duration of the ingestion phase(s) lasts at least 20 days, preferably at least 21 days and in the perimenopause only one ingestion period occurs; that from a time before the (probable) end of the perimenopause and extending into the postmenopause the ingestion phases are successive extended in a transition phase; that permanent administration of hormone daily units commences with advancing postmenopause; and that there is only one ingestion period in the established postmenopause.

It can also be provided that the hormone replacement therapy takes place during the perimenopause in accordance with the ingestion diagram $\{E[1-a]P[d-e]\}$, in which [1-a] means an ingestion phase with hormone daily units having a predeterminable content of at least one estrogen (E) [d-e], an ingestion pause in which administration either takes place of no daily units or placebos (P) or daily units with a much lower hormone content than during the ingestion phase(s) and a, d and e are integers for which a is approximately equal to 21, d is greater by 1 than a and e s equal to or greater than d.

It can also be provided that the hormone replacement therapy during the perimenopause takes place according to the ingestion diagram $\{G[1-a]P[d-e]\}$, in which [1-a] represents an ingestion phase with hormone daily units with a predeterminable content of at least one gestagen (G) and [d-e] an ingestion pause in which either no daily units or placebos (P) or daily units with a much lower hormone content than during the ingestion phase(s) are administered and a, d and e are integers for which a is approximately equal to 21, d is greater by 1 than a and e is equal to or greater than d.

It can also be provided that hormone replacement therapy during the perimenopause takes place according to the ingestion diagram $\{E[1-a]G[b-c]P[d-e]\}$, in which [1-a] represents an ingestion phase with hormone daily units having a predeterminable content of at least one estrogen (E), [b-c] an ingestion phase with hormone daily units with a predeterminable content of at least one gestagen (G) and [d-e] an ingestion pause, in which administration takes place either of no daily units or placebos (P) or daily units with a much lower hormone content than during the ingestion phase(s) and a, b, c, d and e are integers, where a and c are approximately equal to 21, but not necessarily completely equal, b is equal to or greater than 1 and at a maximum is 1 greater than a and equal to or smaller than c, d is the maximum of a and c increased by 1 and e is equal to or greater than d.

It can also be provided that hormone administration takes place during the transition phase according to the diagram $\{E[1-a1]P[d1-e1]\}\{E[1-a2]P[d2-e2]\}$ . . . $\{E[1-ak]P[dk-ek]\}$, in which [1-a1], [1-a2] and [1-ak] ingestion phases with hormone daily units with a predeterminable content of at least one estrogen (E) and [d1-e1], [d2-e2] and [dk-ek] ingestion pauses, in which administration takes place either of no daily units or placebos (P) or daily units with a much lower hormone content than during the ingestion phase(s) and ai, di and ei are integers, where ai is equal to or smaller than aj, if i is smaller than j, d1 is 1 greater than ai and ei is equal to or greater than di, with i, j=1, 2 . . . , k and k is equal to or greater than 1.

It can also be provided that hormone administration takes place during the transition phase according to the diagram $\{G[1-a1]P[d1-e1]\}\{G[1-a2]P[d2-e2]\}$ . . . $\{G[1-ak]P[dk-ek]\}$, in which [1-a1], [1-a2] and [1-ak] ingestion phases with hormone daily units with a predeterminable content of at least one gestagen (G) and [d1-e1], [d2-d2] and [dk-dk] ingestion pauses, in which administration takes place either of no daily units or placebos (P) or daily units with a much lower hormone content than during the ingestion phase(s) and ai, di and ei are integers where ai is equal to or smaller than aj, if i is smaller than j, di is 1 greater than ai and ei is equal to or greater than di, with i, j=1, 2 . . . , k and k is equal to or greater than 1.

It can also be provided that hormone administration during the transition phase takes place according to the diagram $\{E[1-a1]G[b1-c1]P[d1-e1]\}\{E[1-a2]G[b2-c2]P[d2-e2]\}$ . . . $\{[1-ak]G[bk-ck]P[dk-ek]\}$, in which [1-a1], [1-a2], . . . , [1-ak] are ingestion phases with hormone daily units with a predeterminable content of at least one estrogen (E), [b1-c1], [b2-c2], . . . , [bk-ck] ingestion phases with hormone daily units with a predeterminable content of at least one gestagen (G) and [d1-e1], [d2-e2], . . . , [dk-ek] ingestion pauses, in which either no daily units or placebos (P) or daily units with a much lower hormone content than during the ingestion phase(s) are administered and ai, bi, ci, di and ei are integers for which ai is equal to or smaller than aj, if i is smaller than j, ai is approximately equal to ci, bi is at the most 1 greater than ai, the time interval bi-ci is at least half as long and typically not significantly shorter than the time interval 1-ai, di is the maximum increased by 1 of ai and ci and ei is an integer equal to or greater than di, with i, j=1, 2 . . . , k and k is equal to or greater than 1.

It can also be provided that hormone administration during the postmenopause takes place according to the diagram $\{E[1-a]\}$, in which [1-a] signifies an ingestion phase with hormone daily units having a predeterminable content of at least one estrogen (E) and a is a random integer equal to or greater than 1.

It can also be provided that hormone administration during the postmenopause takes place according to the diagram $\{G[1-a]\}$, in which [1-a] signifies an ingestion phase with hormone daily units having a predeterminable content of at least one gestagen (G) and a is a random integer equal to or greater than 1.

It can finally be provided that hormone administration during the postmenopause takes place according to the diagram $\{E[1-a]G[1-a]\}$, in which [1-a] signifies an ingestion phase with hormone daily units having a predeterminable content of at least one estrogen (E) and [1-a] signifies an ingestion phase with hormone daily units having a predeterminable content of at least one gestagen (G) and a is a random integer equal to or greater than 1.

The administration form according to the invention is characterized in that at least one of the packaging units has at least one set of daily units to be administered within an ingestion period, preceding permanent hormone administration, with at least one ingestion phase and at least one ingestion pause, which form an ingestion cycle and comprising a number of hormone daily units corresponding to the duration of the ingestion phase(s) and optionally a number of placebos or daily units, corresponding to the duration of the ingestion pause(s) with a much lower hormone content than in the hormone daily units to be administered in the ingestion phase(s).

It can be provided that there at least three packaging units, whereof a first has at least one set of hormone daily units to be continuously administered at least in the established post-menopause and a second at least two sets of daily units to be administered in the ingestion period(s) preceding permanent hormone administration, the duration of the ingestion phases in the aforementioned ingestion periods successively increasing between the individual ingestion periods.

It can also be provided that the second of the packaging units has at least three sets of daily units corresponding to the ingestion periods preceding continuous hormone administration.

It can also be provided that each set of daily units, corresponding to the ingestion periods preceding continuous hormone administration, comprises a maximum of two daily units corresponding to ingestion cycles.

There can also be an administration forms which is characterized by a plurality of packaging units having at least one set of daily units to be administered during the perimenopause, at least one set of daily units to be administered during the transition phase and at least one set of daily units to be administered during the postmenopause.

It can also be provided that hormone replacement therapy during the perimenopause takes place according to the ingestion diagram $\{E[1-a]P[d-e]\}$, in which [1-a] stands for an ingestion phase with hormone daily units having a predeterminable content of at least one estrogen (E), [d-e] (=) stands for an ingestion pause, in which administration takes place either of no daily units or placebos (P) or daily units with a much lower hormone content than during the ingestion phase(s) and a, d and e are integers, where a is approximately equal to 21, d is 1 greater than a and e is equal to or greater than d.

It can also be provided that hormone replacement therapy during the perimenopause takes place according to the ingestion diagram $\{G[1-a]P[d-e]\}$, in which [1-a] signifies an ingestion phase with hormone daily units having a predeterminable content of at least one gestagen (G) and [d-e] signifies an ingestion pause, in which either no daily units or placebos (P) or daily units with a much lower hormone content than during the ingestion phase(s) are administered and a, d and e are integers where a is approximately equal to 21, d is 1 greater than a and e is equal to or greater than d.

It can also be provided that hormone replacement therapy during the perimenopause takes place according to the ingestion diagram $\{E[1-a]G[b-c]P[d-e]\}$, in which [1-a] signifies an ingestion phase with hormone daily units having a predeterminable content of at least one estrogen (E), [b-c] signifies an ingestion phase with hormone daily units having a predeterminable content of at least one gestagen (G) and [d-e] stands for an ingestion pause in which either no daily units or placebos (P) or daily units with a much lower hormone content than during the ingestion phase(s) are administered and a, b, c, d and e are integers where a and c are approximately equal but not necessarily completely equal to 21, b is equal to or greater than 1 and at a maximum 1 greater than a and equal to or smaller than c, d is the maximum increased by 1 of a and c, and e is equal to or greater than d.

It can also be provided that hormone administration during the transition phase takes place according to the diagram $\{E[1-a1]P[d1-e1]\}\{E[1-a2]P[d2-e2]\}$ . . . $\{E[1-ak]P[dk-ek]\}$, in which [1-a1], [1-a2] and [1-ak] stand for ingestion phases with hormone daily units having a predeterminable content of at least one estrogen (E) and [d1-e1], [d2-e2] and [dk-ek] signify ingestion pauses, in which either no daily units or placebos (P) or daily units with a much lower hormone content than during the ingestion phase(s) are administered and ai, di and ei are integers for which ai is equal to or smaller than aj, if i is smaller than j, d1 is 1 greater than ai and ei is equal to or greater than di, with i, j=1, 2 . . . , k, and k is equal to or greater than 1.

It can also be provided that hormone administration during the transition phase takes place according to the diagram $\{G[1-a1]P[d1-e1]\}\{G[1-a2]P[d2-e2]\}$ . . . $\{G[1-ak]P[dk-ek]\}$, in which [1-a1], [1-a2] and [1-ak] signify ingestion phases with hormone daily units having a predeterminable content of at least one gestagen (G) and [d1-e1], [d2-e2], . . . , [dk-ek] signify ingestion pauses, in which either no daily units or placebos (P) or daily units with a much lower hormone content than during the ingestion phase(s) are administered and ai, di and ei are integers for which ai is equal to or greater than aj, if i is smaller than j, di is 1 greater than ai and ei is equal to or greater than di, with i, j=1, 2 . . . k, and k is equal to or greater than 1.

It can also be provided that hormone administration during the transition phase takes place according to the diagram $\{E[1-a1]G[b1-c1]P[d1-e1]\}\{e[1-a2]G[b2-c2]P[d2-e2]\}$ . . . $\{E[1-ak]G[bk-ck]P[dk-ek]\}$, in which [1-a1], [1-a2], . . . , [1-ak] signify ingestion phases with hormone daily units with a predeterminable content of at least one estrogen (E), [b1-c1], [b2-c2], . . . , [bk-ck] signify ingestion phases with hormone daily units having a predeterminable content of at least one gestagen (G) and [d1-e1][d2-e2], . . . , [dk-ek] signify ingestion pauses, in which either no daily units or placebos (P) or daily units with a much lower hormone content than during the ingestion phase(s) are administered and ai, bi, ci, di and ei are integers for which ai is equal to or smaller than aj, if i is smaller than j, ai is approximately equal to ci, bi is at the maximum 1 greater than ai, the time interval bi-ci is at least half as long as and typically not significantly shorter than the time interval 1-aj, di is the maximum increased by 1 of ai and ci and ei is an integer equal to or greater than di, with i, j=1, 2 . . . , k, and k is equal to or greater than 1.

It can also be provided that hormone administration during the postmenopause takes place according to the diagram $\{E[1-a]\}$, in which [1-a] signifies an ingestion phase with hormone daily units having a predeterminable content of at least one estrogen (E) and a is a random integer equal to or greater than 1.

It can also be provided that hormone administration during the postmenopause takes place according to the diagram $\{G[1-a]\}$, in which [1-a] signifies an ingestion phase with hormone daily units having a predeterminable content of at least one gestagen (G) and a is a random integer equal to or greater than 1.

Finally, it can be provided that hormone administration during the postmenopause takes place according to the diagram $\{E[1-a]G[1-a]\}$, in which [1-a] signifies an ingestion phase with hormone daily units having a predeterminable content of at least one estrogen (E) and [1-a] signifies an ingestion phase with hormone daily units having a predeterminable content of at least one gestagen (G) and a is a random integer equal to or greater than 1.

It is pointed out that the perimenopause can last up to five years and in particular can cover the age period between 45 and 50. The start of the transition phase is approximately two years before the end of the perimenopause and extends approximately 1 to 2 years into the postmenopause. In the specific application case of the method according to the invention the woman and the treating doctor will decide when which ingestion period according to the invention is to be used. This is frequently dependent on the individual menstrual cycle stability and the wishes of the woman concerning the frequency of bleeding. In the present patent the term "transition phase" defines the time interval during which the perimenopause is coming to an end and the postmenopause commences.

The invention is based on the surprising finding that it is possible to avoid the above-described disadvantages of the known regimes, in that during the perimenopause use is made of a sequential regime with an ingestion-free period, prior to the (probable) end of the perimenopause and extending into the postmenopause (transition phase), in which the ingestion phases are successively extended and where a continuous ingestion takes place during the postmenopause.

During the transition phase the ingestion phases are successively extended, so that there is a decrease in the number of withdrawal bleedings per time interval. The cycles are extended in the case of a forecastable cycle length and shorter withdrawal bleeding rates. Menopausal complaints are further reduced. During the postmenopause a continuous ingestion takes place in order to bring about natural amenorrhoea accompanied by reduced intermenstrual bleeding, a simultaneous reduction of menopausal complaints and optionally osteoporosis prevention.

Menopausal complaints are caused by the reduced formation of natural estrogens. The reduction starts before the perimenopause, is greatest during the perimenopause and into the postmenopause and disappears during the postmenopause. According to the invention, during the transition phase, not only are the ingestion time intervals increased, but also the estrogen and gestagen dosages are modified. The duration of the ingestion periods is not a priori fixed. The ingestion period provided for the perimenopause should end before the time when the menopause would occur if hormone replacement therapy was not used. The ingestion period provided for the postmenopause must commence after the time when the menopause would occur if hormone replacement therapy was not used. The ingestion periods for the transition phase occur between these.

In principle, the method can also be used in women who commence hormone replacement therapy during the postmenopause. As no menstrual cycle stabilization is necessary, an ingestion diagram should immediately be started in the form actually provided for the transition phase.

Suitable estrogens with their daily dosages for oral administration (choosing equivalent dosages for other administration forms, such as e.g. plasters or ointments) in the case of hormone daily units intended for administration during ingestion phases, are 0.5 to 6 mg of estradiol (E2), 0.5 to 6 mg estradiol valerate (EV), 0.5 to 6 mg estriol, 0.25 to 3 mg conjugate estrogens, 0.01 to 0.005 mg ethinyl estradiol (EE), 0.05 to 0.8 mg estrogen sulphamates or 0.025 to 0.05 mg mestranol.

Suitable gestagens with their daily dosages for oral administration (here again equivalent dosages are to be chosen for other administration forms, such as e.g. plasters or ointments) are 0.5 to 3 mg chlormadinone acetate (CMA), 1 to 3 mg cyproterone acetate (CPA), 0.05 to 0.2 mg desogestrel (DSG), 1 to 3 mg dienogest (DN6), 0.035 to 0.1 mg gestoden (GSD), 0.025 to 0.5 mg levonorgestrel (LNG), 0.25 to 3.0 mg lynestrenol (LYN), 10 to 200 mg medroxyprogesterone acetate (MPA), 0.175 to 1.5 mg norethisterone (NET), 0.1 to 0.3 mg norgestimate (NGM), 0.015 to 0.75 mg norgestrel (NG), 0.25 to 3 mg norethisterone acetate (NETA), 100 to 300 mg norethisterone anthate (NETE) or 1.5 to 4 mg drospirenone (DRSP).

Suitable combinations of an estrogen and a gestagen, in the case of oral administration and where once again equivalent dosages are to be used if other administration forms, such as e.g. plasters or ointments are employed, are 1 mg cyproterone acetate (CPA) and 2 mg estradiol valerate (EV), or 0.25 mg levonorgestrel (LNG) and 1 mg estradiol valerate (EV), or 0.05 mg gestoden (GSD) and 1 mg estradiol (E2), or 0.05 mg gestoden (GSD) and 2 mg estradiol (E2), or 2 mg drospirenone (DRSP) and 1 mg estradiol (E2), or 3 mg drospirenone (DRSP) and 2 mg estradiol (E2), to give only a few examples.

The administration of the dosage units takes place in such a way that the dosage units of a single ingestion cycle are bundled. If application is e.g. to take place with tablets, the tablets for a single ingestion cycle could be administered in one blister. The bundle or bundles required for an ingestion period are offered in a pack. The packs for different ingestion periods are clearly marked as such. As the number of ingestion cycles for long ingestion periods, particularly the final period, are too large for one pack, the number of bundles contained will be based on circumstances not predetermined by the method.

Further features and advantages of the invention can be gathered from the following description of examples.

EXAMPLE 1

During the perimenopause ingestion takes place according to the diagram {E[1-21]P[22-28]}, during the transition phase according to the diagram {E[1-42]P[43-49]} and during the postmenopause there is a continuous administration of hormone daily units with an estrogen dosage suitable for hormone replacement therapy. Thus, the latter represents a continuous daily ingestion of an estrogen alone.

EXAMPLE 2

During the perimenopause ingestion takes place according to the ingestion diagram {G[1-24]P[25-28]} and during the transition phase according to the diagram {G[1-30]P[31-36]}{G'[1-60]P[61-66]} where, also hereinafter, the apostrophe stands for different dosages. A gestagen is continuously administered during the postmenopause.

EXAMPLE 3

During the perimenopause ingestion takes place according to the diagram {E[1-21]G[4-28]P[29-32]} and during the transition phase according to diagram {E[1-49]G[3-49]P[50-56]}{E'[1-77]G'[2-77]P[78-83]}{E"[1-105]P[106-110]}. During the postmenopause in combination an estrogen and a gestagen are administered daily.

EXAMPLE 4

In the case of women starting hormone replacement therapy during the postmenopause and where consequently no menstrual cycle stabilization was necessary, there is a start with the ingestion period {E[1-42]G[1-42]P[1-42], followed by {E[1-42]G[1-42], which represents a continuous hormone ingestion.

EXAMPLE 5

In a hormone replacement therapy corresponding to example 4 starting with ingestion period {E[1-30]G[6-30]P

[31-36]} and followed by a dosage-reduced, ingestion period {E'[1-60]G'[6-60]P[61-66]} and then a further dosage-reduced ingestion period {E"[1-30]G"[1-30]}, this represents a continuous hormone ingestion.

EXAMPLE 6

In a hormone replacement therapy corresponding to examples 4 and 5, the start is constituted by the ingestion period {E[1-49]G[3-49]P[50-56]}, which is followed by a dosage-reduced, ingestion period {E'[1-77]G'[2-77]P[78-83]}, then a further dosage-reduced ingestion period {E"[1-105]G"[1-105]P[106-110]} and then the ingestion period {E"'[1-105]G"[1-105]} and the ingestion period {E'"[1-105]G"'[1-105], which represents a continuous hormone ingestion.

In examples 4, 5 and 6 the number of ingestion periods, such as is actually provided for the transition phase, is limited to a maximum of 3 and each comprises one or at the most two ingestion cycles.

EXAMPLE 7

EV=Estradiol Valerate

| Perimenopause: | {(2 mg EV)[1-21](1 mg CPA)[1-21]P[22-28]} |
|---|---|
| Transition phase: | {(2 mg EV)[1-42](1 mg CPA)[1-42]P[43-49]} |
| Postmenopause: | {(2 mg EV)[1-42](1 mg CPA)[1-42]} |

EXAMPLE 8

| Perimenopause: | {(2 mg E2)[1-21](0.05 mg GSD)[1-21]P[122-28]} |
|---|---|
| Transition phase: | {(2 mg E2)[1-42](0.05 mg GSD)[1-42]P[43-49]} |
| | {(2 mg E2)[1-66](0.05 mg GSD)[1-66]P[67-73]} |
| Postmenopause: | {(2 mg E2)[1-66](0.05 mg GSD)[1-66]} |

The dosage units are administered as follows. The packs for the perimenopause contain 6 blisters with in each case 21 tablets, the packs for the first ingestion period of the transition phase contain 4 blisters with in each case 42 tablets, the packs for the second ingestion period of the transition phase contain 3 blisters with in each case 66 tablets and the packs for the postmenopause contain 3 blisters with in each case 66 tablets.

EXAMPLE 9

| Perimenopause: | {(2 mg E2)[1-24](3 mg DRSP)[1-24]P[25-28]} |
|---|---|
| Transition phase: | {(2 mg E2)[1-48](3 mg DRSP)[1048]P[49-52]} |
| | {(2 mg E2)[1-72](3 mg DRSP)[1-72]P[73-76]} |
| | {(2 mg E2)[1-96](3 mg DRSP)[1-96]P[97-100]} |
| Postmenopause: | {(2 mg E2)[1-96](3 mg DRSP)[1-96]} |

EXAMPLE 10

ES=Estradiol Sulphamate

| Perimenopause: | {(0.1 mg ES)[1-25]P[26-30]} |
|---|---|
| Transition phase: | {(0.1 mg ES)[1-40]P[41-44]} |
| | {(0.1 mg ES)[1-70]P[71-73]} |
| Postmenopause: | {(0.1 mg ES)[1-90]} |

The features of the invention disclosed in the preceding description and in the claims can be essential to the implementation of the different embodiments of the invention, either singly or in random combination.

What is claimed is:

1. A method for hormone replacement therapy in a female in need thereof having a (B) postmenopause period and
   a (A) preceding period in which said female is in need of HRT, and which comprises at least one ingestion period during which at least one hormone component comprising at least one estrogen (E) and/or at least one gestagen (G) compound is administered,
   comprising in the established (B) postmenopause period of said patient, every day permanently and continuously administering a daily unit with at least one hormonal component comprising at least one estrogen (E) and/or at least one gestagen (G) component, and
   in at least one ingestion period during said (A) preceding period in which said female is in need of HRT, providing an (y) ingestion pause (P), and administering during said pause no daily units, placebos or daily units with a much lower estrogen and/or gestagen content than the content thereof used during the permanent administration of hormone daily units in the established (B) postmenopause period and during the (x) ingestion phase(s) of said ingestion period wherein said (A) preceding period comprises at least two ingestion periods having (x) ingestion phases which are successively extended with respect to each other.

2. A method according to claim 1, wherein the permanent administration of hormone daily units in the (B) postmenopause period is preceded by three ingestion periods, having (x) ingestion phases which are successively extended with respect to each other.

3. A method according to claim 1, wherein each of the ingestion periods preceding the permanent administration of hormone daily units in the (B) postmenopause period, comprises a maximum of two ingestion periods, said periods having in each case one (x) ingestion phase and in each case one (y) ingestion pause.

4. A method of hormone replacement therapy in a female in need thereof having a (C) perimenopause period followed by a (D) transition period and then a (B) postmenopause period in which said female is in need of hormone replacement therapy comprising:
   i) administering during an (x) ingestion phase of the (C) perimenopause period a daily hormone unit in a plurality of substantially time-unlimited, successive ingestion periods, said ingestion periods in an optionally multi-year sequence, having in each case:
      (a) at least one ingestion cycle having a multiday, duration-constant (x) ingestion phase wherein a daily hormone unit is administered for at least 20 days and
      (b) a multiday (y) ingestion pause, ii) administering a daily hormone unit during the (x) ingestion phase of a (D) transition ingestion period, said (D) transition ingestion period having an (x) ingestion phase and an (y) ingestion pause, wherein the (D) transition (x) ingestion phase is longer than all (C) perimenopause (x) ingestion phases, iii) optionally administering a daily hormone unit during the (x) ingestion phase of additional ingestion periods during said transition period, said additional transition ingestion periods each having an (x) ingestion phase and an (y) ingestion pause, in which each additional (x) ingestion phase is longer than in any preceding (x) ingestion phase, and iv) continuously and permanently administering a daily hormone unit during the permanent (B) postmenopause period wherein said hormone unit comprises one E and/ or one G component and wherein said (y) ingestion pauses comprise no daily unit, a placebo or a daily unit with lower E and or G content than in the daily hormone unit administered in the permanent (B) postmenopause period and in the (x) ingestion phase of the corresponding ingestion period.

5. A method according to claim 4, wherein the hormone replacement therapy during the (C) perimenopause period takes place according to the ingestion diagram' {G[1-a]P [d-e]}, in which [1-a] represents an (x) ingestion phase with hormone daily units with a predeterminable content of at least one gestagen (G) and [d-e] an (y) ingestion pause in which either no daily units or placebos (P) or daily units with a much lower hormone content than during the (x) ingestion phase(s) are administered and a, d and e are integers for which a is approximately equal to 21, d is greater by 1 than a and e is equal to or greater than d.

6. A method according to claim 4, wherein hormone replacement therapy during the (C) perimenopause period takes place according to the ingestion diagram {E[1-a]G[b-c]P[d-e]}, in which [1-a] represents an (x) ingestion phase with hormone daily units having a predeterminable content of at least one estrogen (E), [b-c] an (x) ingestion phase with hormone daily units with a predeterminable content of at least one gestagen (G) and [d-e] an (y) ingestion pause, in which administration takes place either of no daily units or placebos (P) or daily units with a much lower hormone content than during the (x) ingestion phase(s) and a, b, c, d and e are integers, where a and c are approximately equal to 21, but not necessarily completely equal, b is equal to or greater than 1 and at a maximum is 1 greater than a and equal to or smaller than c, d is the maximum of a and c increased by 1 and e is equal to or greater than d.

7. A method according to claim 4, wherein hormone administration takes place during the (D) transition phase period according to the diagram {E[1-a1]P[d1-e1]} {E[1-a2]P[d2-e2]} ... {E[1-ak]P[dk-ek]}, in which [1-a1], [1-a2] and [1-ak] (x) ingestion phases with hormone daily units with a predeterminable content of at least one estrogen (E) and [d1-e1], [d2-e2] and [dk-ek] (y) ingestion pauses, in which administration takes place either of no daily units or placebos (P)' or daily units with a much lower hormone content than during the (x) ingestion phase(s) and ai, di and ei are integers, where ai is equal to or smaller than aj, if i is smaller than j, d1 is 1 greater than ai and ei is equal to or greater than di, with i, j=1, 2 ..., k and k is equal to or greater than 1.

8. A method according to claim 4, wherein hormone administration takes place during the (D) transition period according to the diagram {G[1-a1]P[d1-e1]} {G[1-a2]P[d2-e2]} ... {G[1-ak]P[dk-ek]}, in which [1-a1], [1-a2] and [1-ak] (x) ingestion phases with hormone daily units with a predeterminable content of at least one gestagen (G) and [di-e1], [d2-d2] and [dk-dk] (y) ingestion pauses, in which administration takes place either of no daily units or placebos (P) or daily units; with a much lower hormone content than during the (x) ingestion phase(s) and ai, di and ei are integers where ai is equal to or smaller than aj, if i is smaller than j, di is 1 greater than ai and ei is equal to or greater than di, with i, j=1, 2 ..., k and k is equal to or greater than 1.

9. A method according to claim 4, wherein hormone administration during the (D) transition period takes place to the diagram {E[1-a1]G[b1c1]P[d1-e1]}{E[1-a2]G[b2-c2]P [d2-e2]} ... {[1-ak]G[bk-ck]P[dk-ek]}, in which [1-a1], [1-a2], ..., [1-ak] are (x) ingestion phases with hormone daily units with a predeterminable content of at least one estrogen (E), [b1-c1], ... [b2-c2], ... [bk-ck] (x) ingestion phases with hormone daily units with a predeterminable content of at least one gestagen, (G) and [d1-e1].[d2-e2], ..., [dk-ek] (y) ingestion pauses, in which either no daily units or placebos (P) or daily units with a much lower hormone content than during the (x) ingestion phase(s) are administered and ai, bi, ci, di and ei are integers for which ai is equal to or smaller than aj, if i is smaller than j, ai is approximately equal to ci, bi is at the most 1 greater than ai, the time interval bi-ci is at least half as long and typically not significantly shorter than the time interval 1-ai, di is the maximum increased by I of ai and ci and ei is an integer equal to or greater than di, with i, j=1, 2 ..., k and k is equal to or greater than 1.

10. A method according to claim 4, wherein hormone administration during the (B) postmenopause period takes place according to the diagram {E[1-a]}, in which [1-a] indicates an (x) ingestion phase with hormone daily units with a predeterminable content of at least one estrogen (E) and a is a random integer equal to or greater than 1.

11. A method according to claim 4, wherein hormone administration during the (B) postmenopause period takes place according to the diagram {G[1-a]}, in which [1-a] indicates an (x) ingestion phase with hormone daily units having a predeterminable content of at least one gestagen (G) and a is a random integer equal to or greater than 1.

12. A method according to claim 4, wherein hormone administration during the (B) postmenopause period takes place according to the diagram {E[1-a]G[1-a]}, in which [1-a] indicates an (x) ingestion phase with hormone daily units having a predeterminable content of at least, one estrogen (E) and [1-a] indicates an (x) ingestion phase with hormone daily units having a predeterminable content of at least one gestagen (G) and a is a random integer equal to or greater than 1.

13. An administration form for hormone replacement therapy for performing the method according to claim 1, having a plurality of packaging units comprising:

a) at least one packaging unit having at least one set of hormone daily units to be continuously administered at least during the established (B) postmenopause period, in each case having a content of at least one hormonal component, which is at least one estrogen (E) and/or at least one gestagen (G), and b) at least one packaging unit comprising at least one set of daily units to be administered within an ingestion period of said (A) preceding period, which precedes said established postmenopause hormone administration, wherein said (A) preceding ingestion period comprises at least one (x) ingestion phase and at least one (y) ingestion pause, which form an ingestion period, which covers a number of hormone daily units corresponding to the duration of the (x) ingestion phase(s) and optionally a number of placebos or daily units, corresponding to the duration of the (y) ingestion pause(s) which have a much lower hormone content than in the hormone daily units administered in the (x) ingestion phase(s).

14. An administration form according to claim 13, wherein at least three packaging units are provided, wherein a first packaging unit has at least one set of hormone daily units to be continuously administered at least in the established (B) postmenopause period and a second packaging unit having at least two sets of daily units to be administered in the (A) preceding ingestion period(s) which precede the permanent (B) postmenopause period hormone administration, the duration of the (x) ingestion phases in said ingestion periods successively increasing between the individual ingestion periods.

15. An administration form according to claim 14, wherein the second of the packaging units has at least three sets of daily units corresponding to the ingestion periods prior to the continuous hormone administration of said (B) postmenopause period.

16. An administration form according to claim 15, wherein each set of daily units corresponding to (A) preceding ingestion periods which precede the continuous (B) postmenopause period hormone administration comprise a maximum of two daily units corresponding to ingestion periods.

17. An administration form according to claim 13, comprising a plurality of packaging units, having at least one set of daily units to be administered during the (C) perimenopause period, at least one set of daily units to be administered during the (D) transition period and at least one set of daily units to be administered during the (B) postmenopause period.

18. An administration form according to claim 17, wherein hormone replacement therapy during the (C) perimenopause period takes place according to the ingestion diagram {E[1-a]P[d-e]}, in which [1-a] stands for an (x) ingestion phase with hormone daily units having a predeterminable content of at least one estrogen (E), [d-e] stands for an (y) ingestion pause, in which administration takes place either of no daily units or placebos (P) or daily units with a much lower hormone content than during the (x) ingestion phase(s) and a, d and e are integers, where a is approximately equal to 21, d is 1 greater than a and e is equal to or greater than d.

19. An administration form according to claim 17, wherein hormone replacement therapy during the (C) perimenopause period takes place according to the ingestion diagram {G[1-a]P[d-e]}, in which [1-a] signifies an (x) ingestion phase with hormone daily units having a predeterminable content of at least one gestagen (G) and [d-e] signifies an (y) ingestion pause, in which either no daily units or placebos (P) or daily units with a much lower hormone content than during the (x) ingestion phase(s) are administered and a, d and e are integers where a is approximately equal to 21, d is 1 greater than a and e is equal to or greater than d.

20. An administration form according to claim 17, wherein hormone replacement therapy during the (C) perimenopause period takes place according to the ingestion diagram {E[1-a]G[b-c]P[d-eJ}, in which [1-a] signifies an (x) ingestion phase with hormone daily units having a predeterminable content of at least one estrogen (E), [b-c] signifies an (x) ingestion phase with hormone daily units having a predeterminable content of at least one gestagen (G) and [d-e] stands for an (y) ingestion pause in which either no daily units or placebos (P) or daily units with a much lower hormone content than during the (x) ingestion phase(s) are administered and a, b, c, d and e are integers where a and c are approximately equal but, not necessarily completely equal to 21, b is equal to or greater than 1 and at a maximum 1 greater than a and equal to or smaller than c, d is the maximum increased by 1 of a and c, and e is equal to or greater than d.

21. An administration form according to claim 17, wherein hormone administration during the (D) transition period takes place according to the diagram {E[1-a1]P[d1=e1]} {E[1-a2]P[d2-e2]} {E[1-ak]P[dk-ek]}, in which [1-ai], [1-a2] and [1-ak] stand for (x) ingestion phases with hormone daily units having a predeterminable content of at least one estrogen (E) and [d1-e1], [d2-e2] and [dk-ek] signify (y) ingestion pauses, in which either no daily units or placebos (P) or daily, units with a much lower hormone content than during the (x) ingestion phase(s) are administered and ai, di and ei are integers for which ai is equal to or smaller than aj, if i is smaller than j, d1 is 1 greater than ai and ei is equal to or greater than di, with i, j=1, 2 . . . , k, and k is equal to or greater than 1.

22. An administration form according to claim 17, wherein hormone administration during the (D) transition period takes place according to the diagram {G[1-a1]P[d1-e1]} {G[1-a2]P[d2-e2]} . . . {G[1-ak]P[dk-ek]}, in which [1-a1], [1-a2] and [1-ak] signify (x) ingestion phases with hormone daily units having a predeterminable content of at least one gestagen (G) and [di-e1], [d2-e2], . . . , [dk-ek] signify (y) ingestion pauses, in which either no daily units or placebos (P) or daily units with a much lower hormone content than during the (x) ingestion phase(s) are administered and ai, di and ei are integers for which ai is equal to or greater than aj, if i is smaller than j, di is I greater than ai and ei is equal to or greater than di, with i, j=1, 2 . . . , k, and k is equal to or greater than 1.

23. An administration form according to claim 17, wherein hormone administration during the (D) transition period takes place according to the diagram {E[1-a1]G[b1-c1]P[d1-e1]} {e[1-a2]G[b2-c2]P[d2-e2]} . . . {E[1-ak]G[bk-ck]P[dk-ek]}, in which [1-a1], [1-a2], . . . , [1-ak] signify (x) ingestion phases with hormone daily units with a predeterminable content of at least one estrogen (E), [b1-ci], [b2-c2], . . . , [bk-ck] signify (x) ingestion phases with hormone daily units having a predeterminable content of at least one gestagen (G) and [d1-e1] [d2-e2], . . . , [dk-ek] signify (y) ingestion pauses, in which either no daily units or placebos (P) or daily units with a much lower hormone content than during the (x) ingestion phase(s) are administered and ai, bi, ci, di and ei are integers for which ai is equal to or smaller than aj, if i is smaller than j, ai is approximately equal to ci, bi is at the maximum 1 greater than ai, the time interval bi-ci is at least half as long as and typically not significantly shorter than the time interval 1-aj, di is the maximum increased by 1 of ai and ci and ei is an integer equal to or greater than di, with i, j=1, 2 . . . , k, and k is equal to or greater than 1.

24. An administration form according to claim 17, wherein hormone administration during the postmenopause takes place according to the diagram {E[1-a]}, in which [1-a] signifies an (x) ingestion phase with hormone daily units having a predeterminable content of at least one estrogen (E) and a is a random integer equal to or greater than 1.

25. An administration form according to claim 17, wherein hormone administration during the (B) postmenopause period takes place according to the diagram {G[1-a]}, in which [1-a] signifies an ingestion phase with hormone daily units having a predeterminable content of at least one gestagen (G) and a is a random integer equal to or greater than 1.

26. An administration form according to claim 17, wherein hormone administration during the (B) postmenopause period takes place according to the diagram {E[1-a]G[1-a]}, in which [1-a] signifies an ingestion phase with hormone daily units having a predeterminable content of at least one estrogen (E) and [1-a] signifies an ingestion phase with hormone daily units having a predeterminable content of at least one gestagen (G) and a is a random integer equal to or greater than 1.

27. A method of hormone replacement therapy in a female in need thereof having a (A) perimenopause period and a (B) postmenopause period in both of which said female is in need of hormone replacement therapy comprising:
   i) administering a daily hormone unit during the (x) ingestion phase of at least one (C) perimenopause ingestion period, said (C) perimenopause ingestion period having an (x) ingestion phase and an (y) ingestion pause,
   ii) administering a daily hormone unit during the (x) ingestion phase of a (D) transition ingestion period occurring before said (B) postmenopause period, said (D) transition ingestion period having an (x) ingestion phase and an (y) ingestion pause, wherein the (D) transition (x) ingestion phase is longer than the (C) perimenopause (x) ingestion phase,
   iii) optionally administering a daily hormone unit during the (x) ingestion phase of subsequent additional ingestion periods of said transition phase, said additional ingestion periods each having an (x) ingestion phase and an (y) ingestion pause, in which each additional (x) ingestion phase is longer then in any preceding (x) ingestion phase, and
   iv) continuously and permanently administering a daily hormone unit during said (B) postmenopause period wherein said hormone unit comprises one E and/or one G component and
   wherein said (y) ingestion pause comprises no daily unit, a placebo or a daily unit with has lower E and or G content then in the daily hormone unit administered in the permanent (B) postmenopause period and in the (x) ingestion phase of the corresponding ingestion period.

28. A method of hormone replacement therapy according to claim 27, wherein the E and/or G dosage amounts administered in each (x) ingestion phases of ii) and/or iii) are different.

29. A method according to claim 4, wherein the hormone replacement: therapy takes place during the (C) perimenopause period in accordance with the ingestion diagram {E[1-a]P[d-e]}, in which [1-a] means an (x) ingestion phase with hormone daily units having a predeterminable content of at least one estrogen (E) and [d-e] means an (y) ingestion pause in which administration either takes place of no daily units or placebos (P) or daily units with a much lower hormone content than during the (x) ingestion phase(s) and a, d and e are integers for which a is approximately equal to 21, d is greater by I than a and e is equal to or greater than d.

30. A method according to claim 4, wherein the duration of the (x) ingestion phase(s) is at least 21 days.

31. A method of hormone replacement therapy according to claim 4, wherein the E and/or G dosage amounts administered in each (x) ingestion phases of ii) and/or iii) are different.

* * * * *

UNITED STATES PATENT AND TRADEMARK OFFICE
CERTIFICATE OF CORRECTION

| | | |
|---|---|---|
| PATENT NO. | : 7,871,994 B2 | |
| APPLICATION NO. | : 10/466197 | |
| DATED | : January 18, 2011 | |
| INVENTOR(S) | : Kulmann | |

It is certified that error appears in the above-identified patent and that said Letters Patent is hereby corrected as shown below:

Column 11, line 51 reads "administration takes place during the (D) transition phase" should read -- administration takes place during the (D) transition --

Signed and Sealed this
Fifth Day of April, 2011

David J. Kappos
*Director of the United States Patent and Trademark Office*